United States Patent
Kim et al.

(10) Patent No.: US 9,795,746 B2
(45) Date of Patent: Oct. 24, 2017

(54) FILTER NEEDLE

(71) Applicant: Dongguk University Industry—Academic Cooperation Foundation, Seoul (KR)

(72) Inventors: Sung Min Kim, Gyeonggi-do (KR); Ho Chul Kang, Gyeonggi-do (KR)

(73) Assignee: Dongguk University Industry—Academic Cooperation Foundation, Seoul (KR)

( * ) Notice: Subject to any disclaimer, the term of this patent is extended or adjusted under 35 U.S.C. 154(b) by 218 days.

(21) Appl. No.: 14/431,738

(22) PCT Filed: Oct. 30, 2014

(86) PCT No.: PCT/KR2014/010279
§ 371 (c)(1),
(2) Date: Mar. 26, 2015

(87) PCT Pub. No.: WO2015/102218
PCT Pub. Date: Jul. 9, 2015

(65) Prior Publication Data
US 2016/0256635 A1    Sep. 8, 2016

(30) Foreign Application Priority Data

Jan. 3, 2014  (KR) .................... 10-2014-0000784
Oct. 28, 2014  (KR) .................... 10-2014-0147232

(51) Int. Cl.
*A61M 5/34*         (2006.01)
*A61M 39/24*        (2006.01)
(Continued)

(52) U.S. Cl.
CPC .......... *A61M 5/345* (2013.01); *A61M 5/3145* (2013.01); *A61M 39/223* (2013.01);
(Continued)

(58) Field of Classification Search
CPC ............... A61M 5/345; A61M 5/3145; A61M 2005/3114; A61M 39/24; A61M 2039/2406; A61M 2005/3128
See application file for complete search history.

(56) References Cited

U.S. PATENT DOCUMENTS

| 9,265,883 B2 * | 2/2016 | Kim ...................... A61M 5/165 |
| 2011/0208128 A1 * | 8/2011 | Wu ....................... A61J 1/2096 |
|  |  | 604/247 |

(Continued)

FOREIGN PATENT DOCUMENTS

| KR | 10-2012-0114742 A | 10/2012 |
| KR | 10-2012-0114746 A | 10/2012 |

(Continued)

OTHER PUBLICATIONS

Korean Application No. 10-2014-0147232, Office Action dated Oct. 10, 2010, with English Translation, 11 pgs.

*Primary Examiner* — Nathan R Price
*Assistant Examiner* — Courtney Fredrickson
(74) *Attorney, Agent, or Firm* — Schwegman Lundberg & Woessner, P.A.

(57) ABSTRACT

The present relates to a filter needle coupled between a fixation member having a needle for injecting a medical fluid after filtering foreign substances contained in the medical fluid and a disposable syringe, the filter needle includes an outer housing having a front end portion to which the fixation member is coupled and a rear end portion to which the disposable syringe is coupled and a filtering unit which is disposed inside the outer housing, and in which a medical fluid supplied from the fixation member to the disposable syringe is passed through as is, while a medical fluid supplied from the disposable syringe to the fixation member is filtered.

8 Claims, 7 Drawing Sheets

(51) Int. Cl.
*A61M 5/31* (2006.01)
*A61M 39/22* (2006.01)

(52) U.S. Cl.
CPC ..... *A61M 39/24* (2013.01); *A61M 2005/3114* (2013.01); *A61M 2005/3128* (2013.01); *A61M 2039/2406* (2013.01); *A61M 2205/7545* (2013.01)

(56) References Cited

U.S. PATENT DOCUMENTS

2014/0213982 A1    7/2014  Kim et al.
2015/0045738 A1    2/2015  Kim

FOREIGN PATENT DOCUMENTS

| KR | 10-1222881 B | 1/2013 |
| KR | 10-1287239 B1 | 7/2013 |
| KR | 10-2013-0139812 A | 12/2013 |
| WO | WO-2013152179 A1 | 10/2013 |

* cited by examiner

FILTER NEEDLE

CROSS-REFERENCE TO RELATED APPLICATIONS

This application is a U.S. National Stage Filing being made under 35 U.S.C. §371 from International Application Serial No. PCT/KR2014/010279, entitled "FILTER NEEDLE," filed on Oct. 30, 2014, which claims the benefit of priority under 35 U.S.C. §119 to Korean Patent Application No. 10-2014-0000784 filed Jan. 3, 2014, and to Korean Patent Application No. 10-2014-0147232, filed on and Oct. 28, 2014, the disclosures of which are incorporated herein by reference in their entireties.

BACKGROUND OF THE INVENTION

Field of the Invention

The present invention relates to a filter needle, and more particularly to a filter needle, which is used by being mounted to a front end of a syringe or to a three-way stop cock, and in which foreign substances inside a syringe or a Ringer solution are filtered when a medical fluid is injected into a human body from an ampule or a Ringer's solution, thereby having enhanced convenience and safety.

Description of the Related Art

In general, syringes are used for injecting a substance into an infected patient, and disposable syringes are usually used to prevent the occurrence of a secondary infection. Such disposable syringes inject a mixture of a medical fluid and a powder or only a medical fluid.

In this case, the medical fluid is contained in an ampule, which is usually made of glass or plastic. Thus, foreign substances such as glass powder or plastic powder are generated at a section of the ampule when the ampule is opened.

The ampule is mostly made of glass in many cases to prevent contamination during storage and transportation. A medical fluid in the ampule is suctioned in such a way that an inlet is formed by breaking a portion of the ampule or a syringe needle is forcibly inserted into a rubber plug. In this process, fine glass powder or fine rubber particles are mixed into the medical fluid and introduced into a syringe.

When medical fluid containing such foreign substances is sucked into a syringe, there is a problem in that many adverse effects are produced for patients when such medical fluids are injected.

To solve the above-mentioned problem, a filter has recently been proposed, which is installed in a needle fixing member and filters foreign substances, such as glass, when a medical fluid is sucked into a cylinder through the syringe needle. However, there is a problem in that the foreign substances adhered to the filter are directly injected again into patients in the case of direct injection into patients without syringe needle replacement.

Accordingly, at an actual medical site, a filter-mounted syringe needle is used when filling a syringe by suctioning a medical fluid, and a method of injection after the syringe needle is replaced with a new one is used when the medical fluid is injected into a patient after filling the medical fluid.

Such a series of operations is very cumbersome in the administering of injections to patients, and the quick treatment of emergency patients is not possible. Also, a great number of disposable syringes are used in a day, and because a plurality of syringe needles are used for injections, medical waste is geometrically increased, thereby having an adverse effect on the environment.

Moreover, since this medical waste is processed after being separated from general waste, the problem of increased costs for processing arises.

SUMMARY OF THE INVENTION

An aspect of the present invention provides a filter needle in which foreign substances can be completely filtered through a filter during an injection even though the foreign substances are introduced when filling a syringe with a medical fluid, and also, a medical fluid can be injected into a patient without replacing the syringe needle even in a state in which the syringe is filled with the medical fluid.

According to an aspect of the present invention, there is provided a filter needle characterized by including: an outer housing having a front end portion to which the fixation member is coupled and a rear end portion to which the disposable syringe is coupled and a filtering unit which is disposed inside the outer housing, and in which a medical fluid supplied from the fixation member to the disposable syringe is passed through as is, while a medical fluid supplied from the disposable syringe to the fixation member is filtered.

According to another aspect of the present invention, the filtering unit may include: an inner housing movably disposed inside the outer housing to move to front and rear ends of the outer housing; an opening/closing member which is coupled to an inner portion of the inner housing and comprises an opening/closing part having an opening/closing hole extending to a front end portion of the inner housing and opening/closing an opening portion of the outer housing; a filter disposed at a rear end portion of the opening/closing member to filter a medical fluid; and a coupling member coupled to a rear end portion of the inner housing.

The filtering unit may open the opening portion of the outer housing as being moved to the rear end portion of the outer housing through a suctioning force during suctioning by the disposable syringe, and may thus supply the medical fluid, introduced from the fixation member to the outer housing, as is to the disposable syringe, and the filtering unit may close the opening portion of the outer housing as being moved to the front end portion of the outer housing by a compression force during compressing by the disposable syringe, filter the medical fluid, introduced from the disposable syringe to the outer housing, through the filter, and supply the medical fluid to the fixation member through the opening/closing hole of the opening/closing member.

The opening/closing member may be formed of a rubber having elasticity and may be disposed in a cone shape having a diameter that gradually increases in a direction from a front end portion to a rear end portion thereof.

The opening/closing hole may be maintained in a sealed state by a closely adhering force due to elasticity thereof, and when a pressure of a medical fluid is generated from a rear end portion of the opening/closing member, the opening/closing hole may be gradually expanded to pass the medical fluid therethrough.

One or more first passageways may be formed in a length direction on an outer surface of the inner housing.

The outer housing may contain the filter unit and may include an outer case having an injection hole at a front end portion thereof, and a finishing member coupled to a rear end portion of the outer case.

The finishing member may have a support portion which supports the filter unit and also has a medical fluid passageway through which a medical fluid passes.

The finishing member may have a luer lock which is coupled to a groove of the disposable syringe.

BRIEF DESCRIPTION OF THE DRAWINGS

The above and other aspects, features and other advantages of the present invention will be more clearly understood from the following detailed description taken in conjunction with the accompanying drawings, in which:

FIGS. 5 and 6 are views illustrating a state in which the filter needle with the above-mentioned configuration according to an embodiment of the present invention is used, where

DETAILED DESCRIPTION OF THE PREFERRED EMBODIMENT

Exemplary embodiments of the present invention will be described with reference to the accompanying drawings so as to sufficiently understand constitutions and effects of the present invention. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. In the drawings, the shapes of components or the like may be exaggerated for clarity. It is also noted that like reference numerals in the drawings refer to like elements. Moreover, detailed descriptions related to well-known functions or configurations will not be included in order not to unnecessarily obscure subject matters of the present invention.

A filter needle according to preferred embodiments of the present invention will be described below in more detail with reference to the accompanying drawings. The filter needle may be defined as a filter between a fixation member having a needle and a syringe.

Figure 1:
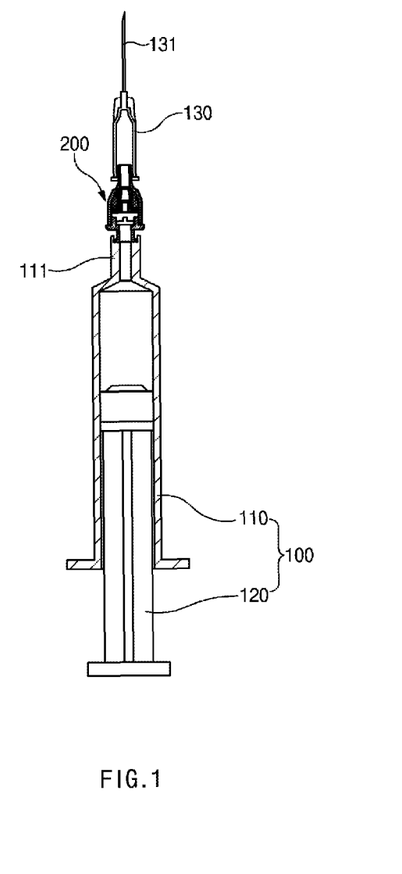
FIG. 1 is a cross-sectional view illustrating a disposable syringe having a filter needle according to an embodiment of the present invention.
Figure 2:
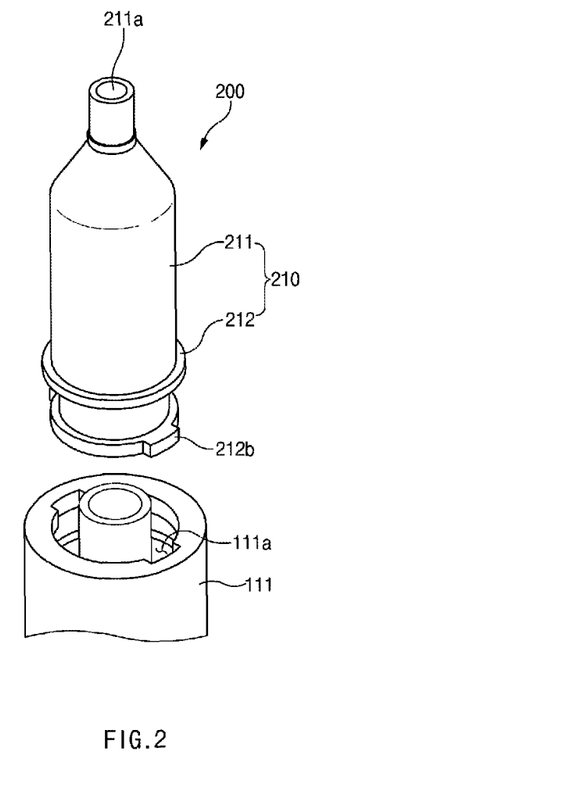
FIG. 2 is a perspective view illustrating the filter needle of FIG. 1.
Figure 3:
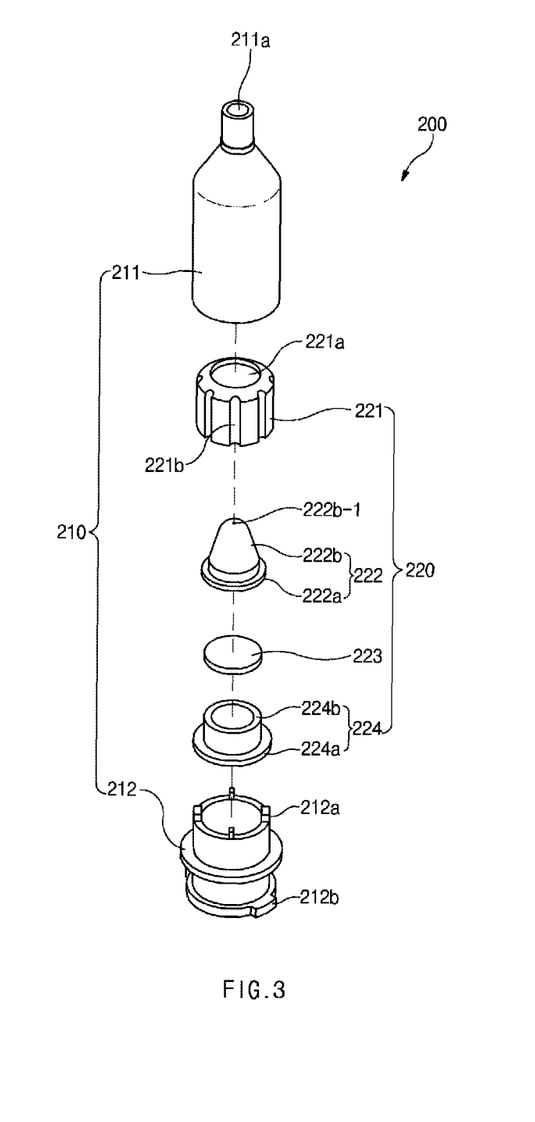
FIG. 3 is an exploded perspective view of FIG. 2.
Figure 4:
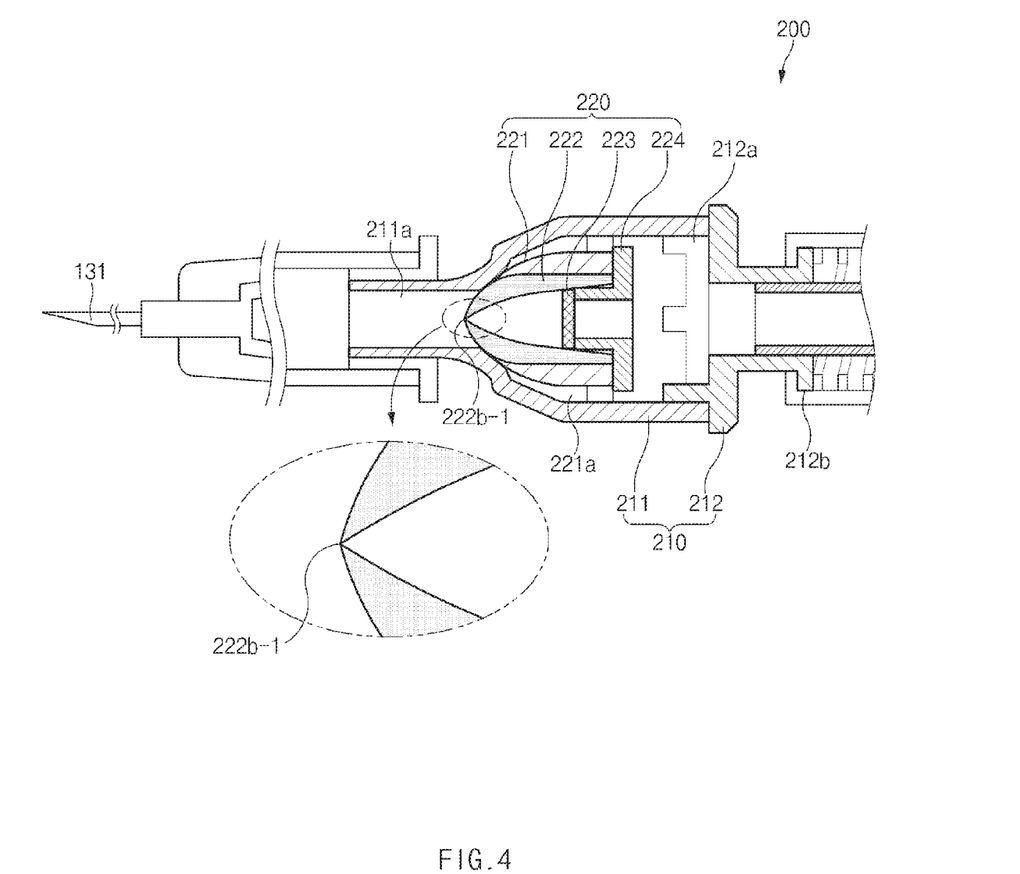
FIG. 4 is a cross-sectional view of FIG. 2.

FIG. 1 is a cross-sectional view illustrating a disposable syringe having a filter needle according to an embodiment of the present invention, FIG. 2 is a perspective view illustrating the filter needle of FIG. 1, FIG. 3 is an exploded perspective view of FIG. 2, and FIG. 4 is a cross-sectional view of FIG. 2.

Referring to FIG. 1, the syringe 100 according to an embodiment of the present invention includes: a syringe cylinder 110 which is provided for forcibly suctioning or forcibly discharging a medical fluid, and in which the medical fluid is stored in the syringe cylinder; a syringe piston 120 for compressing and discharging the medical fluid, wherein a fixation member 130 having a medical fluid container (not shown) containing the medical fluid or a needle 131 for injection into a human body is connected to an injection opening 111 of the syringe cylinder 110.

Foreign substances may be contained in the medical fluid stored in the medical fluid container. When a medical fluid containing foreign substances is injected into a human body, and particularly, when a medical fluid containing foreign substances which are harmful to the human body is injected into a human body, a medical accident may result.

To prevent this, the filter needle 200 is included in the syringe 100 according to an embodiment of the present invention so that a medical fluid, in which foreign substances are filtered, may be injected into a human body. Referring to FIGS. 1 and 2, the filter needle 200 is disposed between the disposable syringe 100 and the fixation member 130 having a needle 131, and filters the medical fluid supplied from the disposable syringe 100 to the needle 131, so that the medical fluid, which now contains no foreign substances, may be injected into a human body through the needle 131.

That is, as illustrated in FIGS. 2 through 4, the filter needle 200 according to an embodiment of the present invention includes: an outer housing 210, which is coupled between a fixation member having a needle for injecting a medical fluid after filtering foreign substances contained in the medical fluid, and has a front end portion to which the fixation member 130 is coupled and a rear end portion to which an opening 111 of the syringe cylinder 110 is coupled; and a filter unit 220 which filters the medical fluid introduced from the syringe cylinder 110 to the outer housing 210, and supplies the medical fluid to the needle 131 of the fixation member 130.

The outer housing 210 is one for connecting the fixation member having the needle and the disposable syringe, has a cylindrical shape, and includes an outer case 211 having a front end portion in which an opening portion 211a coupled to the fixation member 130 is formed and a finishing member 212 which is coupled to an rear end portion of the outer case 211 and to which the disposable syringe is coupled.

Also, a luer lock 212b, which is coupled to a coupling groove 111a of the disposable syringe, is formed at a rear end portion of the finishing member 212. The coupling performance of the filter needle 200 and the disposable syringe may be enhanced by the luer lock 212b, such that various kinds of disposable syringes may be compatibly used.

The filtering unit 220 is disposed inside the outer housing, and has a structure in which, on the one hand, a medical fluid supplied from the fixation member to the disposable syringe 100 is directly passed through and, on the other hand, a medical fluid supplied from the disposable syringe to the fixation member 130 is filtered.

That is, the filtering unit 220 does not filter the medical fluid suctioned from the medical fluid container to the disposable syringe 100, while the medical fluid discharged from the disposable syringe 100 to the medical fluid container is filtered.

For instance, the filtering unit 220 includes an inner housing 221, an opening/closing member 222, a filter 223, and a coupling member 224.

The inner housing 221 is disposed inside the outer housing 210, moves in a length direction of the outer housing—that is, in a direction from a front end portion to a rear end portion—and defines a through-hole 221a at the front end portion.

Also, one or more first passageways 221b are defined in a length direction on an outer surface of the inner housing 221. The first passageways 221b are medical fluid passageways defined between the inner housing 221 and the outer housing 210, and may induce a smoother movement of the medical fluid.

Figure 5:
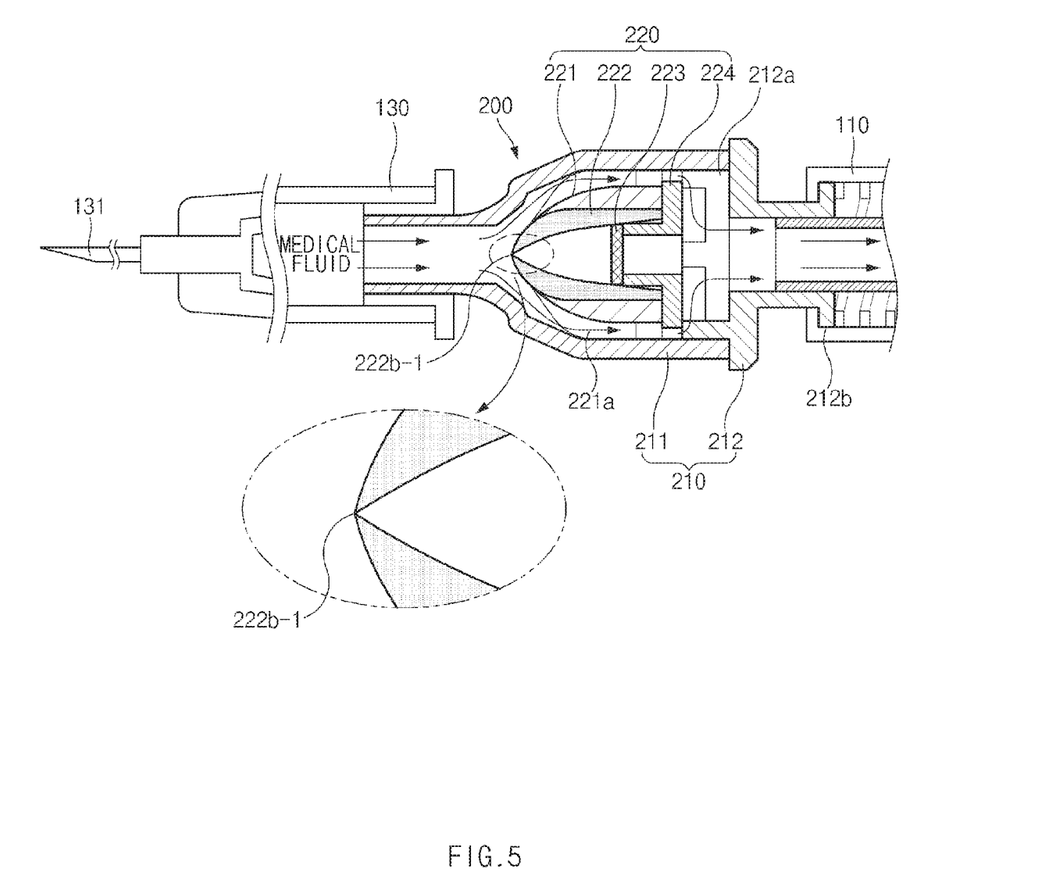
FIG. 5 is a view illustrating an operating state of the filter needle during suctioning by a syringe piston.
Figure 6:
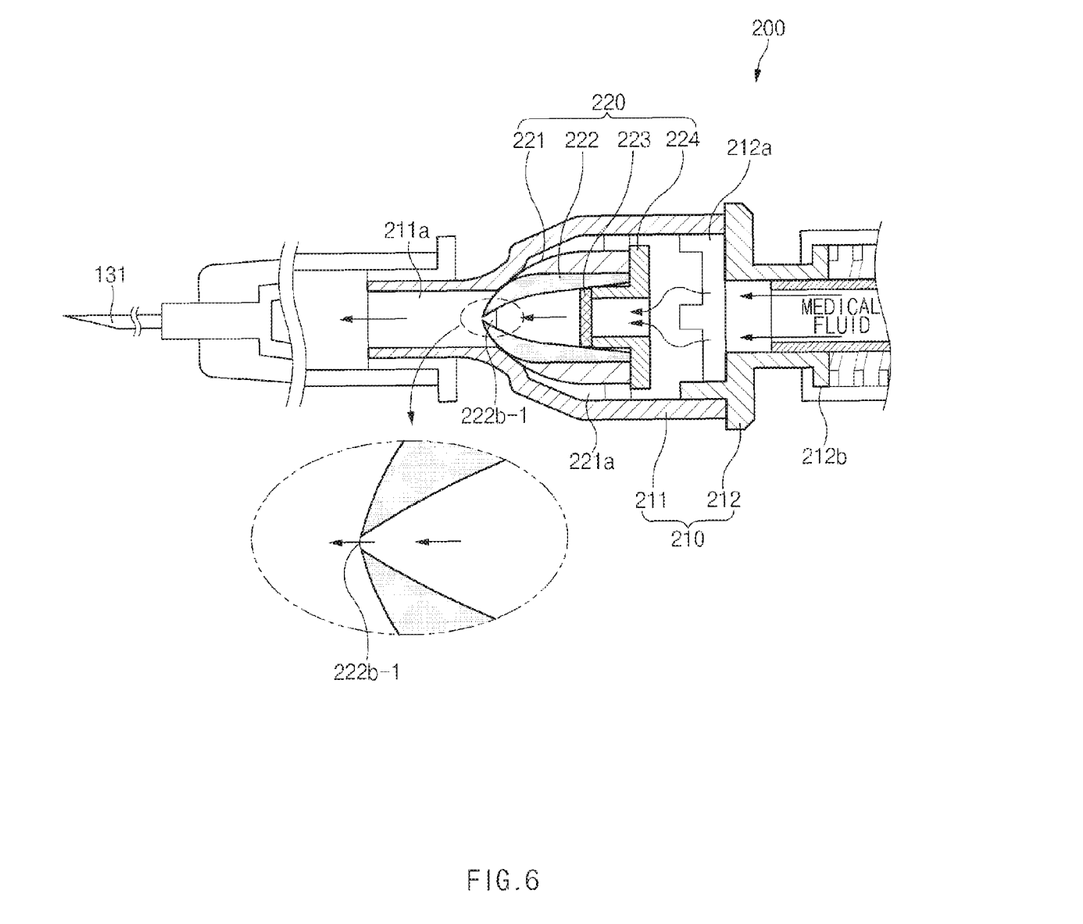
FIG. 6 is a view illustrating an operating state of the filter needle during compression by a syringe piston.

That is, in the inner housing 221, in the case of suctioning by the disposable syringe 100, a medical fluid introduced from the fixation member 130 to the outer housing 210 is supplied to the disposable syringe through the first passageways 221b (See FIG. 5), and in the case of compression by the disposable syringe 100, a medical fluid introduced from the syringe cylinder 110 to the outer housing 210 is supplied to the fixation member 130 through the through-hole 221a (See FIG. 6).

The opening/closing member 222 is one for opening/closing the outer housing according to suctioning or compression by the disposable syringe, and includes an opening/closing rib 222a coupled to an inside of the inner housing 221, and an opening/closing portion 222b which extends from the opening/closing rib 222a, protrudes through the through-hole 221a, and defines an opening/closing hole 222b-1 at a protruding end portion thereof.

Here, the opening/closing member 222 is formed of a cone-shaped nontoxic rubber having elasticity, and disposed in a cone shape in which the width gradually increases in a direction from a front end portion to a rear end portion (from the left side to the right side shown in FIG. 4) thereof.

Here, the opening/closing hole 222b-1 is maintained in a sealed state by a closely adhering force due to the elasticity thereof. At this point, on the one hand, even if the pressure of a medical fluid is generated at the front side of the opening/closing member 222, the opening/closing hole 222b-1 is maintained in a sealed state and, on the other hand, when the pressure of a medical fluid is generated at the rear side of the opening/closing member 222, the opening/closing hole 222b-1 is gradually expanded to pass the medical fluid therethrough.

When the pressure is generated at the front end portion of the outer housing 210, this opening/closing member 222 opens an opening 211a of the outer housing 210 while moving together with the inner housing 221 to the rear end of the outer housing 210 because the pressure cannot pass through the opening/closing hole 222b-1 due to point contact at the front end of the opening/closing hole 222b-1. Here, the pressure is introduced into the disposable syringe through the opening 211a and an outer circumferential surface of the inner housing 221. Next, when the pressure is generated at the rear end portion of the outer housing 210, this opening/closing member 222 closes an opening 211a of the outer housing 210 while moving together with the inner housing 221 to the front end portion of the outer housing 210, and the opening/closing hole 222b-1 is opened while being expanded by the pressure. Thus, the pressure is introduced into the fixation member 130 through the opening/closing hole 222b-1.

The filter 223 is one for filtering foreign substances contained in the medical fluid passing through the inside of the opening/closing member 222, and is disposed inside the inner housing to finish a rear end portion of the opening/closing member 222.

That is, the filter 223 filters foreign substances contained in the medical fluid in such a manner that the medical fluid passes through the filter 223 before passing through the opening/closing hole 222b-1 of the opening/closing member 222.

The coupling member 224 is coupled to the rear end of the inner housing 221, and fixes the opening/closing member 222 and the filter 223 disposed inside the inner housing 221 to not move.

That is, the coupling member 224 includes a coupling rib 224a coupled to the rear end of the inner housing 221, and a coupling portion 224b inserted inside the inner housing 221 to fix the filter 223 and the opening/closing member 222.

Also, the finishing member 212 has a plurality of support portions 212a having a medical fluid passageway through which the medical fluid passing through an outer side of the filtering unit 220 passes.

The filtering unit 220 with this configuration opens the opening portion 211a formed at the front end portion of the outer housing 210 while moving to the rear end of the outer housing 210 by means of a suctioning force during the suctioning of the disposable syringe 200, and thus supplies the medical fluid introduced from the fixation member 130 to the outer housing 210, as is, to the disposable syringe 100. Also, the filtering unit 220 closes the opening portion 211a of the outer housing while moving to the front end of the outer housing 210 by means of a compressing force during the compression of the disposable syringe 200, and thus supplies the medical fluid introduced from the disposable syringe 100 to the outer housing 210 to the fixation member 130 after filtering the medical fluid.

Thus, the filtering unit 220 filters the medical fluid supplied to the needle 131 so that the medical fluid that is free of foreign substances may be injected to a human body, so as to enhance safety.

A state of using the filter needle with the above-mentioned configuration according to an embodiment of the present invention will be described below.

As illustrated in FIG. 5, a filter needle 200 is coupled to a front end portion of a disposable syringe 100, and a fixation member 130 having a needle is coupled to a front end portion of the filter needle 200.

Then, the upper end of an ampule (not shown) is broken, and in a state in which a needle is inserted into the ampule, a syringe piston 120 of the disposable syringe 100 is pulled to suction a medical fluid into a syringe cylinder 110.

At this point, the medical fluid passing through a fixation member 130 pressurizes a filtering unit 220 while being introduced into an outer housing 210 of the filter needle 200, and moves the filter unit 220 to a rear end of the outer housing 210. Thus, the medical fluid and foreign substances, such as glass powder from the ampule, introduced into the outer housing 210 are introduced as is without being filtered into the disposable syringe 100 through a first passageway 221b of an inner housing 221 and a medical fluid passageway of a support portion 212a in the filtering unit 220.

Also, in the filtering unit 220, since a front end portion of an opening/closing hole 222b-1 of an opening/closing member 222 is closed due to a point contact, the medical fluid cannot pass therethrough (see the arrow illustrated in FIG. 5).

Next, when the medical fluid in the ampule is completely introduced inside the syringe cylinder 210 of the disposable syringe 100, a needle 310 is inserted into a human body and then the syringe piston 120 is pressed.

Then, as illustrated in FIG. 6, the medical fluid in the syringe cylinder 210 is inserted into a human body through the filter needle 200 and the needle 131 of the fixation member 130 by means of the pressure of the syringe piston 120.

At this point, an opening portion 211a is closed by means of the pressure of the medical fluid introduced in the outer housing 210 while the filtering unit 220 is moved to the front portion of the outer housing 210. Thus, the medical fluid cannot pass through a space between the filtering unit 220 and the outer housing 210 and is filtered while passing through the filtering unit 220.

That is, the medical fluid introduced into the outer housing is introduced into the inner housing 221 through a coupling member 224, is filtered of foreign substances while passing through a filter 223, and is introduced into the fixation member 130 due to the opening of an opening/closing hole 222b-1 of an opening/closing member 222 by pressurizing a rear portion of the hole.

Hereinafter, in the description of a filter needle according to another embodiment of the present invention, components having the same structures and functions as those in previous embodiments have been given the same reference numerals in the drawings, and duplicated description thereof will not be provided.

Figure 7:
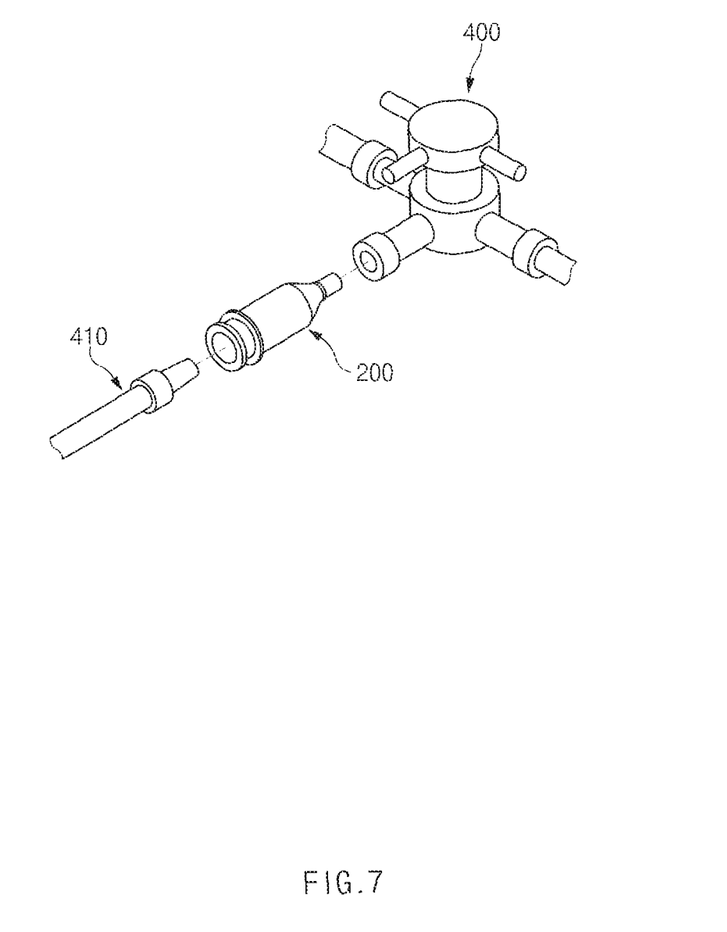
FIG. 7 is a perspective view illustrating a state in which the filter needle according to an embodiment of the present invention is inserted into a three-way stopcock.

FIG. 7 is a perspective view illustrating a state in which the filter needle according to an embodiment of the present invention is inserted into a three-way stopcock.

The filter needle 200 according to an embodiment of the present invention may also be inserted into the three-way cock 400 as illustrated in FIG. 7. Here, since a ringer solution set 410 is insertedly coupled through forced insertion when being inserted into a rear end portion of the filter needle 200, the pressure inside the three-way stop cock 400 and the filter needle 200 is increased. Thus, the opening/closing hole 222b-1 of the opening/closing member 222 may be opened without the application of external pressure. Therefore, the medical fluid filtered through the filter 223 may be injected into a human body through the opening/closing hole 222b-1 and the three-way stopcock 400.

Thus, since a filter needle according to an embodiment of the present invention is constructed as one unit and may be used for any injection-related equipment, the simultaneous injection of foreign substances during an injection of a medical fluid may be prevented, and a medical fluid may be injected into a patient as is without replacing a syringe needle in the process of filling and injecting the medical fluid as in conventional arts, so that convenience and safety are enhanced.

According to the filter needle of the present invention, firstly, the filter needle can be used by being mounted to a general syringe comprising a cylinder and a piston, and particularly, foreign substances are filtered by a filter in the process of filling and injecting a medical fluid, whereby safety can be enhanced.

Secondly, when a medical fluid is injected into a human body, foreign substances, which can be injected together with the medical fluid, can be filtered, and the medical fluid can be injected into a patient as is without replacing a syringe needle in the process of filling and injecting the medical fluid as in conventional arts, whereby convenience and safety can be enhanced.

Thirdly, since passageways for suctioning and discharging a medical fluid are separated, there is no possibility of foreign substances being discharged together with a medical fluid when the medical fluid is discharged. Accordingly, since the medical fluid can be injected after being suctioned without replacing a syringe needle, there are effects in that it is convenient and it is possible to quickly treat an emergency patient.

Fourthly, even if fine foreign substances are contained in a medical fluid suctioned by a syringe, the foreign substances are filtered by a filter included in the filter needle and remain inside the syringe cylinder, and thus, there is absolutely no possibility for foreign substances to be discharged when the medical fluid is injected into a patient, and there is an effect in that a safer treatment is possible.

The above-mentioned description of embodiments of the filter needle according to the present invention is intended to be illustrative, and those with ordinary skill in the technical field to which the present invention pertains will understand that the present invention can be carried out in other specific forms without changing the technical idea or essential features thereof. Thus, it will be well understood that the present invention is not restricted or limited to a form mentioned in the foregoing detailed description. Hence, the real protective scope of the present invention shall be determined by the technical scope of the accompanying Claims. Also, the present invention should be understood to include all changes, equivalents, and alterations within the spirit and scope of the present invention defined by the appended claims.

What is claimed is:

1. A filter needle coupled between a fixation member having a needle and a disposable syringe for injecting a medical fluid after filtering foreign substances contained in the medical fluid, the filter needle being characterized by comprising:

an outer housing having a front end portion to which the fixation member is coupled and a rear end portion to which the disposable syringe is coupled; and a filtering unit which is movably disposed inside the outer housing to move to front and rear ends of the outer housing, wherein when the medical fluid is supplied from the fixation member to the disposable syringe, the filtering unit is moved to the rear end portion of the outer housing through a suctioning force during suctioning by the disposable syringe and an opening portion of the outer housing is opened so that the medical fluid flows around the filtering unit and is supplied to the disposable syringe without being filtered, and wherein when the medical fluid is supplied from the disposable syringe to the fixation member, the filtering unit is moved to the front end portion of the outer housing through a compressing force during compression by the disposable syringe and the opening portion is closed so that the medical fluid is supplied to the fixation member through the filtering unit while being filtered.

2. The filter needle of claim 1, wherein the filtering unit comprises:

an inner housing movably disposed inside the outer housing to move to the front and rear ends of the outer housing;

an opening/closing member which is coupled to an inner portion of the inner housing and comprises an opening/closing part, having an opening/closing incision extending to a front end portion of the inner housing and configured to open/close the opening portion of the outer housing;

a filter disposed at a rear end portion of the opening/closing member to filter the medical fluid supplied from the disposable syringe to the fixation member; and a coupling member coupled to a rear end portion of the inner housing.

3. The filter needle of claim 2, wherein the opening/closing member is formed of a rubber having elasticity, and disposed in a cone shape in which a diameter gradually increases in a direction from a front end portion to a rear end portion thereof.

4. The filter needle of claim 1, wherein when the medical fluid is supplied from the fixation member to the disposable syringe, the opening/closing incision is maintained in a sealed state by a closely adhering force due to elasticity thereof, and when a pressure of the medical fluid supplied from the disposable syringe to the fixation member is generated from a rear end portion of the opening/closing member, the opening/closing incision is gradually expanded to pass the medical fluid therethrough.

5. The filter needle of claim 2, wherein the inner housing comprises at least one first passage formed in a lengthwise direction in an outer surface thereof.

6. The filter needle of claim 1, wherein the outer housing contains the filtering unit and comprises an outer case having an injection hole at a front end portion thereof, and a finishing member coupled to a rear end portion of the outer case.

7. The filter needle of claim 6, wherein the finishing member comprises a support portion which supports the filtering unit and also has a medical fluid passageway through which the medical fluid supplied from the fixation member to the disposable syringe passes through.

8. The filter needle of claim 6, wherein the finishing member comprises a luer lock which is coupled to a coupling groove of the disposable syringe.

* * * * *